United States Patent [19]

Fullenwider

[11] Patent Number: 5,081,420
[45] Date of Patent: Jan. 14, 1992

[54] METHOD AND APPARATUS FOR MEASURING HYDROGEN ION CONCENTRATION AND ACTIVITY IN AN ELECTROLYTE

[76] Inventor: Malcolm A. Fullenwider, P.O. Box 2, Whitehall, Pa. 18052

[21] Appl. No.: 542,010

[22] Filed: Jun. 22, 1990

[51] Int. Cl.⁵ .......................................... G01N 27/56
[52] U.S. Cl. .................................. 324/438; 204/433; 204/400; 204/153.21; 204/153.1; 324/450; 324/71.1
[58] Field of Search ............. 324/438, 439, 425, 71.1, 324/450; 204/433, 400, 153.21, 153.1

[56] References Cited

U.S. PATENT DOCUMENTS 4,028,196 6/1977 Young .......................... 204/153.21
4,516,077 5/1985 Fenneman et al. ............... 324/425
4,644,285 2/1987 Britton ............................. 324/425
4,840,708 6/1989 Puippe ........................... 204/153.1

Primary Examiner—Gerard R. Strecker
Assistant Examiner—Robert W. Mueller
Attorney, Agent, or Firm—Albert L. Free

[57] ABSTRACT

A pH-measuring system using a Barnacle electrode (e.g. Ni—NiO₂) in an electrolyte to abstract hydrogen from a metal electrode in the same electrolyte, and produces data as to the time $t_{max}$ required for the current density at the exposed surface of the metal electrode to reach its maximum value $j_{max}$ after an external circuit between the two electrodes is closed. From $t_{max}$ and $j_{max}$ the pH in the bulk of the electrolytes is determined, for display or for control purposes.

3 Claims, 1 Drawing Sheet

METHOD AND APPARATUS FOR MEASURING HYDROGEN ION CONCENTRATION AND ACTIVITY IN AN ELECTROLYTE

BACKGROUND OF THE INVENTION

The concentration of hydrogen ions, i.e. pH, in the bulk of an electrolyte has been measured in the past using a glass electrode or a three-electrode cell. While useful for many purposes, the present invention provides a third method of such measurement which is believed to be more fundamental in nature, and potentially more accurate in certain situations.

SUMMARY OF THE INVENTION

In accordance with the invention, a so-called Barnacle electrode is used to measure the hydrogen ion concentration at the surface of a metal electrode, e.g. platinum or steel, immersed in a body of electrolyte, with the metal electrode externally connected by electrical conductors to another electrode, e.g. a nickel-nickel oxide electrode, immersed in the same body of electrolyte. This measurement is accomplished by measuring the time at which the current flowing through the external conductors reaches a peak value $t_{max}$ measured from the time at which the external circuit is first completed, as well as the value of the peak current density $j_{max}$ at the surface of the metal (e.g. platinum) electrode. The data as to $t_{max}$ and $j_{max}$ are supplied to a programmed computer to determine the value of pH in the bulk of the electrolyte, remote from the surface of the platinum electrode and from the nickel-nickel oxide electrode. The preferred function relating pH to $t_{max}$ and $t_{max}$, and programmed into the computer, is as follows:

$$pH = 3/2 \log C - \log j_{max} t_{max} + 4.8 \quad (1)$$

This pH meter is suitable for use with a wide range of electrolytes and pH values, including for example pH's from about 14 to about 1 and most electrolytes which will not react chemically with the electrode materials.

Similarly, the metal electrode may be of a variety of material, of which the following are merely examples: platinum, palladium, nickel and iron.

As to the nickel-nickel oxide electrode, this may also take other forms in different applications of the invention; it is only necessary that it be of the type which brings the metal electrode to the reversible hydrogen potential.

In the preferred embodiment of the invention, a Micro-Processor and pH Display Unit is provided which senses the current flowing in the external conductors when the external circuit is closed, which detects the maximum value $j_{max}$ of the current, which utilizes the $t_{max}$ data and $j_{max}$ data derived by the maximum-value sensor to produce an output signal representative of the value of the pH in the bulk electrolyte, and preferably which utilizes the latter signal to produce a visual display of the value of the pH; the pH signal may also be used as a control signal, for any of one of a large variety of control purposes.

BRIEF DESCRIPTION OF FIGURES

These and other objects and features of the invention will be more readily understood from a consideration of the following detailed description, taken with the accompanying drawings, in which.

DETAILED DESCRIPTION OF SPECIFIC EMBODIMENTS

Figure 1:
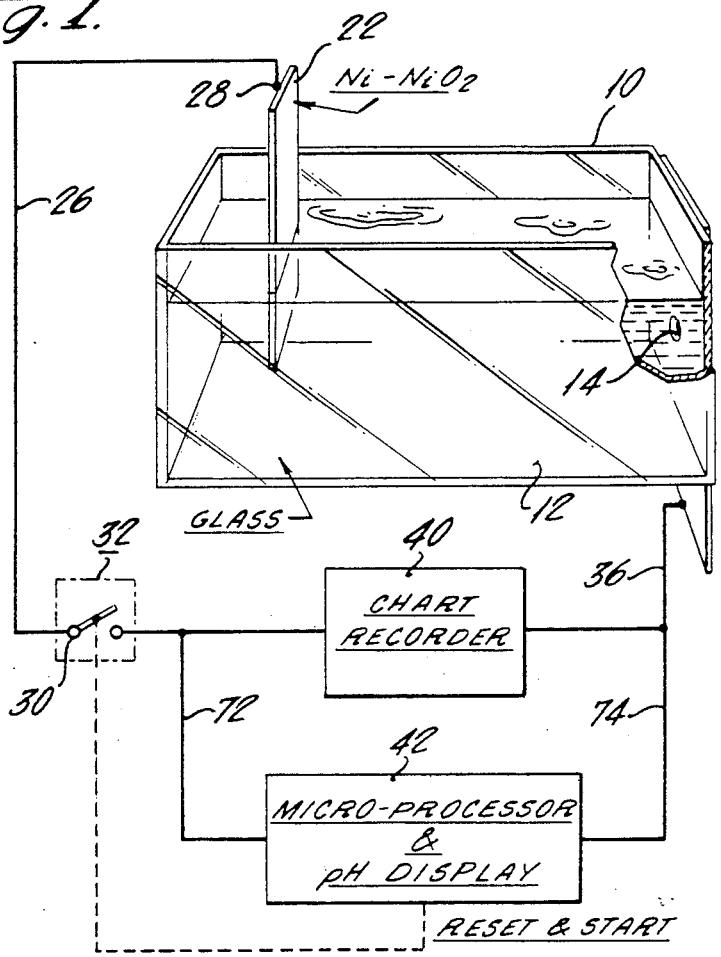
FIG. 1 is a schematic diagram showing apparatus for practicing the invention in one of its embodiments.
Figure 2:
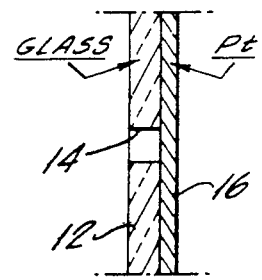
FIG. 2 is a vertical sectional view of one end of a tank containing a body of electrolyte, the wall of the tank having an opening through which a backing layer of a suitable metal, such as is exposed, to the electrolyte.
Figure 3:
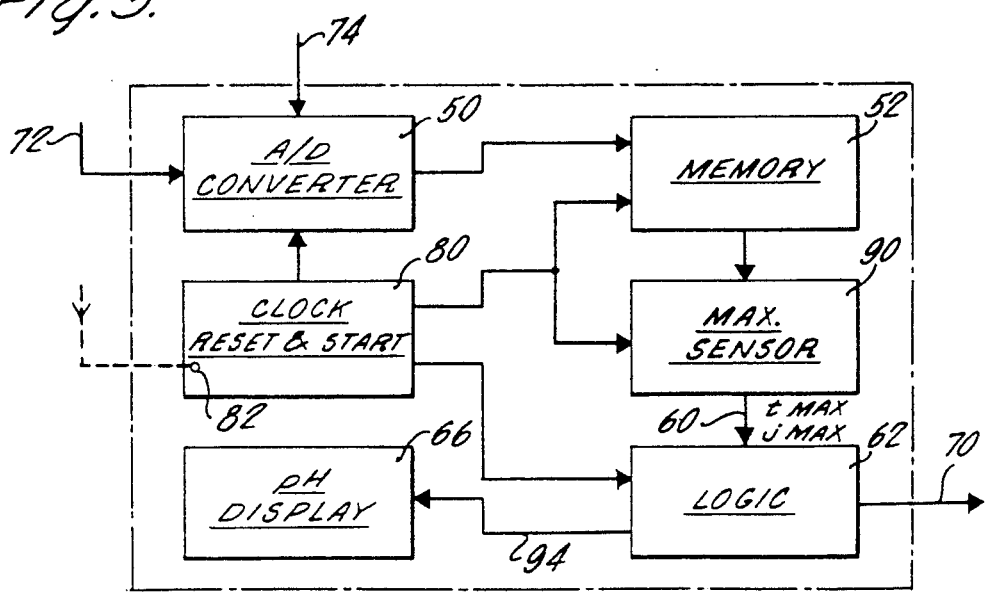
FIG. 3 is a block diagram illustrating a suitable type of Microprocessor and pH Display Unit, responsive to the current flowing in the external circuit to produce a display of pH value and, optionally an output data signal representing the pH value.

Referring now to the specific embodiment now illustrated in the drawings by way of example only, and without thereby in any way limiting the scope of the invention, FIG. 1 shows a tank 10 of inert material, which may be glass. One end 12 of the tank is provided with a circular opening 14, and a metal plate 16 is sealed to the tank end and overlies this opening, as shown in FIG. 2, where it is assumed that the metal plate is platinum, although it could be of any variety of other metals including, for example, steel. The tank 10 contains an electrolyte 20 whose pH is to be measured; in this example it may be 0.1 normal NaOH, and a nickel-nickel-oxide plate 22 is partially immersed in the electrolyte as shown. The nickel-nickel oxide electrode may be formed in known manner, by suitably oxidizing the surface of a nickel plate.

A first electrical conductor 26 is connected at one of its ends 28 to an exterior portion of the nickel-nickel oxide plate, and extends to one terminal 30 of a single-pole, single-throw switch 32; the metal plate 16 is connected, by a second external conductor 32, to the opposite terminal of switch 32, in this example by way of a chart recorder 40 and, in parallel therewith, a Microprocessor and pH Display Unit 42.

In operation, the nickel-nickel oxide plate 22, the metal electrode 16, the conductors 26, 36, the switch 32, the chart recorder 40 and the Microprocessor and pH Display Unit 42 are all connected as shown in FIG. 1, with switch 32 open. When a reading of pH is to be made, the switch 32 is closed, and current immediately begins to flow in the external conductors 26 and 36, in series. The chart recorder 40 is used to produce a convenient visually-observable graph of the varying magnitude of the current immediately following closing of the switch; this current typically will increase to a maximum after a time typically of the order of a few minutes, and then decrease substantially to zero. From this trace, one can visually read the time $t_{max}$ following closing of the switch at which the maximum occurred, as well as the maximum current itself. This current, when adjusted by a scale factor corresponding to the exposed area of electrode 16, provides the current density $j_{max}$ at the exposed surface of electrode 16; in this example, the opening 14 may have an area of one square centimeter, so that, in effect, no such division of the measured current is necessary.

The Microprocessor and pH Display Unit 40 converts the current to digital form, stores the digital current value and time in a memory, senses the maximum stored $j_{max}$ value to produce the current value $j_{max}$, produces the $t_{max}$ signals and, by use of a logic circuit, performs the above-described manipulations indicated by equation 1. This produces a control signal which is used to operate a pH display and to produce a pH data output signal on an output line.

In this example, conductor 72 supplies current from the switch 32 to an input of the A/D converter 50, which is also connected to the other external conductor 74, so that the A/D converter is supplied with information as to the current density $j_{max}$, as it varies as a function of time following the closing of the switch. A suitable digital clock 80 also supplies signals to the A/D converter, and has a Reset and Start terminal 82 such that, when the switch is first closed, the clock is reset to zero and begins to run. The digital output of converter 50 supplies its data to any suitable memory 52, which stores the current density value as a function of time following closing of the switch. A maximum-value sensor 90 is supplied with the contents of memory 52 when clock 80 has counted out a time interval greater than that in which the maximum current value will certainly have occurred. Digital devices for sensing, and retaining an indication of, the maximum value of the signals supplied thereto are well known in the art and need not be described in detail.

The output of the maximum sensor supplies the values of $t_{max}$ and $j_{max}$ to logic 62. Logic 62 performs the calculation indicated by equation 1 above, in order to produce on its output line 94 a signal representing pH, for display on display 66; the another output line 70 provides an external output for the pH-representing signal for any desired purpose, for example to control the addition of acid or other electrolyte components to the electrolyte both, to obtain a desired pH value.

The logic functions required for the calculation of pH may take any of a variety of forms, and may be entirely conventional. Thus equation 1 above has 3 terms, namely (log C), (minus log $j_{max}t_{max}$), and (4.8), to be combined arithmetically. The first term itself is actually a constant once the system has been calibrated. Such calibration may be performed by, for example, placing 0.1 normal NaOH electrolyte in the tank, for which the pH is known to be substantially equal to 13. The values for $j_{max}$ and $t_{max}$ produced by the maximum-value sensor 90 may then be observed and used in formula 1 above, along with substitution of 13 for the value of pH. This gives log $C = 13 + $ (measured value of log $j_{max}t_{max}$) $- 4.8 \times \frac{2}{3}$; C is the antilog of this simple expression. The value of C thus determined is then set into the logic 62 in order for it to perform the desired calculation of pH, given only the $j_{max}$ and $t_{max}$ data from maximum-value sensor 90.

The above-set-forth equation (1) is derived from the following considerations. The time at which the maximum current $t_{max}$ occurs is equal to 8/D, where D is the diffusion coefficient in centimeters square per second. $j_{max}$ in amperes per square centimeter at the metal electrodes surface is equal to $$2.36 D^{\frac{1}{2}} C_o \times 10^5 \div t^{\frac{1}{2}} max,$$

or upon rearrangement of terms, $$C_o = (8/D)^{\frac{1}{2}} j_{max}/D^{\frac{1}{2}} \times 2.36 \times 10^5.$$

where $C_o$ is defined as the original concentration of hydrogen in the metal electrode near its surface.

Now by statistics, in the bulk of the electrolyte (which is in equilibrium with the 2-dimensional surface gas of H ions at the metal electrode surface)

$$C_o^{\frac{3}{2}} = C a_H^{\frac{3}{2}} - 3/2 KTh\, a_H\, e^{W_H/KT}/(2\pi m_H KT)^{\frac{1}{2}} \quad (3)$$

where
$C_o$ = as defined above
$a_H$ = hydrogen activity in the bulk of the electrolyte
K = Boltzmann's constant
T = temperature Kelvin
h = Planck's constant
$W_H$ = the energy of the proton in the metal electrode with respect to infinity dispersion outside
$m_H$ = mass of hydrogen atom.

Since the second term of (3) is generally small compared with the first term, it can be neglected for most cases of pH values from about 14 to about 1, whereby $$a_H^{\frac{3}{2}} = (C_o)^{\frac{3}{2}}/C \quad (4)$$

for the activity in the electrolyte.

Expression (1) above for pH is derived from (4) by dropping the second term on the right hand side of (3), i.e. by assuming the system to be diluted.

Where the electrolyte is more acid than stated above, the value of the second term of equation (3) may be retained and taken into account.

While an Ni—NiO$_2$ electrode is described above as a Barnacle electrode, used to draw the hydrogen from the metal electrode, one may instead use an electrode in a vacuum, monitoring the gas pressure, together with a potentiometer or potentiostat arrangement to provide the appropriate bias for Barnacle operation.

While the invention has been shown and described with particular reference to specific embodiments thereof in the interest of complete definiteness, it will be understood that it may be embodied in other forms diverse from those specifically shown and described, without departing from the scope of the invention as defined by the appended claims.

What is claimed is:

1. Apparatus for measuring the pH of an electrolyte, comprising:
   a metal electrode and means for exposing a predetermined area thereof to said electrolyte;
   a Ni—NiO$_2$ electrode, and means for holding at least a part thereof immersed in said electrolyte;
   a first conductor, electrically connected at one end thereof to said metal electrode;
   a second conductor electrically connected at one end thereof to said Ni—NiO$_2$ electrode;
   switch means for controllably connecting said first conductor to said second conductor and for disconnecting it therefrom, thereby to connect and disconnect said metal electrode and said Ni—NiO$_2$ electrode at will, and to produce a transient current through said conductors after they are connected to each other;
   means responsive to said transient current for producing signals representative of the maximum value $j_{max}$ of said transient current after a closure of said switch means, and signals indicative of the time $t_{max}$ after said closure at which said value $j_{max}$ is attained; and
   computing means responsive to said $t_{max}$ indicating signals and said $j_{max}$—indicating signals for producing a pH-representing signal, having a value given by the following expression:

$$pH = 3/2 \log C - \log j_{max}t_{max} + 4.8,$$

where C is a calibration constant, determinable for any electrode and type of electrolyte.

2. The apparatus of claim 1, wherein said computing means responsive to said $t_{max}$—representing signal and said $j_{max}$—representing signal comprises digital processing apparatus for computing said value of said expression from the values of $j_{max}$ and $t_{max}$.

3. The method of determining the pH of an electrolyte, comprising:

simultaneously exposing to said electrolyte an $N_i$—$N_1O_2$ electrode and a metal electrode;

forming an external connection between said Ni—NiO$_2$ electrode and said metal electrode at any time $t_o$;

measuring the value $j_{max}$ of the current density at the surface of said metal electrode at the time $t_{max}$, measured from $t_o$ at which the transient current flowing through said external connection reaches a maximum value; and inputting the value $j_{max}$ and $t_{max}$ to a computer programmed to calculate the value of pH in said electrolyte remote from each of said electrodes to produce a value of pH substantially equal to 3/2 log C−log $j_{max}t_{max}$+4.8, where C is a calibration constant, determinable for any electrode and type of electrolyte by inserting said electrode in an electrolyte.

* * * * *